(12) United States Patent
Corot

(10) Patent No.: US 8,349,293 B2
(45) Date of Patent: Jan. 8, 2013

(54) USE OF METAL NANOPARTICLES IN THE DIAGNOSIS OF ALZHEIMER'S DISEASE

(75) Inventor: Claire Corot, Lyons (FR)

(73) Assignee: Guerbet, Villepinte (FR)

( * ) Notice: Subject to any disclaimer, the term of this patent is extended or adjusted under 35 U.S.C. 154(b) by 388 days.

(21) Appl. No.: 12/532,353

(22) PCT Filed: Mar. 21, 2008

(86) PCT No.: PCT/EP2008/053450
§ 371 (c)(1),
(2), (4) Date: Nov. 19, 2009

(87) PCT Pub. No.: WO2008/125422
PCT Pub. Date: Oct. 23, 2008

(65) Prior Publication Data
US 2010/0111876 A1    May 6, 2010

(30) Foreign Application Priority Data
Mar. 22, 2007  (FR) ...................................... 07 53980

(51) Int. Cl.
*A61B 5/055* (2006.01)
(52) U.S. Cl. ..................................... 424/9.32; 424/9.321
(58) Field of Classification Search ........................ None
See application file for complete search history.

(56) References Cited

U.S. PATENT DOCUMENTS

| | | | |
|---|---|---|---|
| 5,643,599 A | 7/1997 | Lee et al. | |
| 6,638,494 B1 * | 10/2003 | Pilgrimm | 424/9.323 |
| 2004/0253181 A1 | 12/2004 | Port et al. | |
| 2005/0260137 A1 | 11/2005 | Acar et al. | |
| 2006/0051293 A1 | 3/2006 | Kung et al. | |
| 2007/0090323 A1 | 4/2007 | Duguet et al. | |
| 2008/0206146 A1 | 8/2008 | Akhtari et al. | |
| 2009/0246170 A1 | 10/2009 | Inoue et al. | |

FOREIGN PATENT DOCUMENTS

| | | |
|---|---|---|
| FR | 2 861 994 A1 | 5/2005 |
| WO | WO-02/094191 A2 | 11/2002 |
| WO | WO-03/037351 A1 | 5/2003 |
| WO | WO-2004/058275 A2 | 7/2004 |
| WO | WO-2004/100958 A1 | 11/2004 |
| WO | WO-2004/107368 A2 | 12/2004 |
| WO | WO-2005/014041 A2 | 2/2005 |
| WO | WO-2005/028484 A1 | 3/2005 |
| WO | WO-2005/039586 A1 | 5/2005 |
| WO | WO-2005/040126 A1 | 5/2005 |
| WO | WO-2005/044830 A1 | 5/2005 |
| WO | WO-2005/046563 A2 | 5/2005 |
| WO | WO-2005/092856 A1 | 10/2005 |
| WO | WO-2005/095348 A2 | 10/2005 |
| WO | WO-2005/095361 A1 | 10/2005 |
| WO | WO-2005/095365 A1 | 10/2005 |
| WO | WO-2005/095367 A1 | 10/2005 |
| WO | WO-2005/095368 A1 | 10/2005 |
| WO | WO-2005/097114 A2 | 10/2005 |
| WO | WO-2005/105776 A1 | 11/2005 |
| WO | WO-2006/005580 A1 | 1/2006 |
| WO | WO-2006/012201 A1 | 2/2006 |
| WO | WO-2006/031190 A1 | 3/2006 |
| WO | WO-2006/045430 A1 | 5/2006 |
| WO | WO-2006/066790 A1 | 6/2006 |
| WO | WO-2006/102377 A2 | 9/2006 |
| WO | WO-2006/115416 A2 | 11/2006 |
| WO | WO-2007/020190 A1 | 2/2007 |
| WO | WO-2007/034326 A2 | 3/2007 |
| WO | WO-2007/042421 A1 | 4/2007 |
| WO | WO-2007/069053 A1 | 6/2007 |
| WO | WO-2007/071598 A1 | 6/2007 |
| WO | WO-2007/082806 A1 | 7/2007 |
| WO | WO-2007/088399 A1 | 8/2007 |
| WO | WO-2007/088401 A1 | 8/2007 |
| WO | WO-2007/090720 A2 | 8/2007 |
| WO | WO-2007/098417 A2 | 8/2007 |
| WO | WO-2007/105053 A2 | 9/2007 |
| WO | WO-2007/110335 A1 | 10/2007 |
| WO | WO-2007/110727 A2 | 10/2007 |
| WO | WO-2007/114771 A1 | 10/2007 |
| WO | WO-2007/122274 A1 | 11/2007 |
| WO | WO-2007/123680 A2 | 11/2007 |
| WO | WO-2007/125364 A1 | 11/2007 |
| WO | WO-2007/130383 A2 | 11/2007 |
| WO | WO-2007/132292 A2 | 11/2007 |
| WO | WO-2007/135131 A1 | 11/2007 |
| WO | WO-2007/137954 A1 | 12/2007 |
| WO | WO-2007/138431 A2 | 12/2007 |
| WO | WO-2007/139178 A1 | 12/2007 |
| WO | WO-2007/143523 A2 | 12/2007 |
| WO | WO-2007/145589 A1 | 12/2007 |

OTHER PUBLICATIONS

Product #P9416, Tween20. Sigma-Aldrich. http://www.sigmaaldrich.com. Accessed Jan. 12, 2012.*
Kircher MF, Mahmood U, King RS, Weissleder R, Josephson L. A multimodal nanoparticle for preoperative magnetic resonance imaging and intraoperative optical brain tumor delineation. 2003 Cancer Res. 63: 8122-8125.*
Viroonchatapan E, Sato H, Ueno M, Adachi I, Tazawa K, Horikoshi I. Magnetic targeting of thermosensitive magnetoliposomes to mouse livers in an in situ on-line perfusion system. 1996 Life Sci. 58: 2251-2261.*
Roney C, Kulkarni P, Arora V, Antich P, Bonte F, Wu A, Mallikarjuana NN, Manohar S, Liang HF, Kulkarni AR, Sung HW, Sairam M, Aminabhavi TM. Targeted nanoparticles for drug delivery through the blood-brain barrier for Alzheimer's disease. 2005 J. Control. Release 108: 193-214.*
Pardridge WM. Transport of small molecules through the blood-brain barrier: biology and methodology. 1995 Adv. Drug Deliv. Rev. 15: 5-36.*

* cited by examiner

*Primary Examiner* — Nissa M. Westerberg
*Assistant Examiner* — Jennifer Lamberski
(74) *Attorney, Agent, or Firm* — Birch, Stewart, Kolasch & Birch, LLP

(57) ABSTRACT

The invention relates to the use of metal nanoparticles for the preparation of a composition for diagnosing Alzheimer's disease by MRI.

16 Claims, 1 Drawing Sheet

USE OF METAL NANOPARTICLES IN THE DIAGNOSIS OF ALZHEIMER'S DISEASE

The invention relates to the use of metal nanoparticles, advantageously coated with an organic protective layer, for the diagnosis, advantageously by MRI, of Alzheimer's disease.

Alzheimer's disease (AD) is a neurodegenerative disease characterized by an impairment of cognitive function that combines memory, intellectual function and personality disorders without modification of the state of consciousness. AD exists in 2 forms: a late and sporadic form, the most common, which represents 90% to 95% of currently known cases, and a familial form (autosomial dominant nature) which represents only 5% to 10% of all known cases. Examination of the brain of patients suffering from AD reveals very precise histopathological lesions which are senile plaques (SPs) and neurofibrillary tangles (NFTs).

There is a very large number of SPs in the cerebral cortex of AD patients. They are also found in Trisomy 21 and at varying, generally low, levels during normal brain aging.

On the optical microscopy scale, they are extracellular deposits having a microscopic spherical structure made up of a core of insoluble proteins (amyloid substance) surrounded by degenerated neural extensions. On the electron microscopy scale, the amyloid substance is made up of bundles of straight filaments having a diameter of 6 to 9 nm. These filaments occupy the extracellular domain of the central nervous tissue. On the molecular scale, these protein clusters are essentially made up of the short form of beta-amyloid peptide ($A\beta_{40}$), a polypeptide filament which adopts a sheet structure that gives it its insoluble nature and probably its toxicity. $A\beta$ is the product of the catabolism of a membrane protein precursor, APP (amyloid protein precursor).

The neurofibrillary tangles correspond to the accumulation of pathological fibrils in the cytoplasm of neurons. This is therefore an intraneuronal lesion. It is especially the pyramidal cells of the associative cerebral cortex and of the hippocampal structure that are affected by this phenomenon.

The prior art describes specific compounds that are vectorized, in particular in fluorescence imaging, in MRI (magnetic resonance imaging) or in scintigraphy, which comprise, on the one hand, a signal entity and, on the other hand, a biovector (targeting agent) intended for the specific molecular targeting of a marker overexpressed in Alzheimer's disease, and in particular for targeting amyloid plaques. For example, document US2006051293 describes peptide and nonpeptide targeting ligands coupled to paramagnetic-metal or radionuclide chelates.

The vast majority of publications concern nuclear medicine, which has the advantage of being highly sensitive, but the drawback, in addition to its irradiating nature, of giving low resolution compared with MRI. Document WO02094191 admittedly describes, for MRI, particles denoted MION (monocrystalline), comprising a core of iron oxide, comprising a layer of dextran and coupled to an AD-targeting peptide biovector, but they are peptides that are complex to produce and to couple.

Among the various technical problems to be solved, the applicant has sought compounds which are effective in MRI imaging of Alzheimer's disease, of the metal nanoparticles type, different than the prior art, and in particular metal nanoparticles not vectorized by a specific targeting biovector, with thus the advantage of a synthesis that is less complex and expensive than the vectorized products.

For this, the applicant has worked on nanoparticles which exhibit in particular an improved uptake by the macrophages that are associated with a mechanism of inflammation correlated with AD, and are capable of crossing the BBB (blood-brain barrier). The applicant has also worked on nanoparticles capable of crossing the BBB at least in part directly, via a biological mechanism of passive or active transport, without the necessary intervention of macrophages, through the use of groups facilitating BBB transfer, described in the application.

In the application, the term "macrophage uptake" is used in the interests of simplification, but this term includes the case of uptake by any cell system of the immune system, in particular phagocytic system, associated with AD and involved in an inflammatory/immune process localized in particular at the level of the amyloid plaques or of other affected areas of the brain with activation of phagocytic cells. This involves more especially uptake by monocytes, macrophages, microglia or any other cell type known to those skilled in the art.

According to one aspect, the invention relates more specifically to the use of metal nanoparticles for the preparation of a composition for diagnosis by MRI for the diagnosis of Alzheimer's disease (AD), these particles comprising a core covered with a nonpolymeric layer devoid of AD-specific targeting biovector. This layer makes it possible to protect the core.

The expression "polymeric layer devoid of AD-specific targeting biovector" is intended to mean that the polymeric layer and the nanoparticles do not exhibit any ligands known in the prior art (in particular peptides or antibodies) for specifically targeting AD markers such as amyloid peptides.

According to the invention, grafted onto the nonpolymeric layer devoid of targeting biovector are groups that promote macrophage uptake, such as the hydrophilic groups described in detail hereinafter in the application, and/or polymeric groups that promote BBB transfer. However, these groups do not include the biovectors known in the prior art for specifically recognizing macrophage receptors (in particular SRA receptors).

According to preferred embodiments, the nonpolymeric layer is anionic. Advantageously, it is chosen from the following layers (and also the known derivatives thereof):

phosphate, phosphonate, phosphonate monoester, diphosphonate, bisphosphonate, gem-bisphosphonate, diphosphate, thiophosphate, thiophosphonate, polyphosphate, phosphinate;

sulfonate, bisulfonate;

hydroxamate, arginine hydroxamate;

silane, or silica derivative, silanetriol, siloxane, trialkoxysilane;

amino acid;

mercapto, dimercaptosuccinic acid;

carboxylate, aliphatic dicarboxylic or polycarboxylic acid (malic acid, citric acid, tartaric acid, aspartic acid, gluconic acid, in particular), advantageously an aliphatic acid comprising at least three —COOH, cyclohexanetricarboxylic acid or cyclohexanehexacarboxylic acid functions;

cathecolate.

The silane typically have the formula ($Si_nH_{2n+2}$), the siloxanes the formula R—SiO (for example, $[SiO(CH_3)_2]_n$).

According to embodiments, the polycarboxylic acid comprises at least two carboxylic functions and is chosen from the following acids: citric acid, (D,L) tartaric acid, tartaric acid, glutaric acid, malic acid, cyclohexanetricarboxylic acid, cyclohexanehexacarboxylic acid, ethylediaminetetraacetic acid, diethylenetriaminepentaacetic acid, 4-bromomandelic acid, cis,cis,cis,cis-1,2,3,4-cyclopentanetetracarboxylic acid, DL-malic acid, dibenzoyl-D-tartaric acid, chelidonic acid, tetrahydrofuran-1,3,4,5-tetracarboxylic acid, DL-isocitric acid, mucic acid, oxalic acid and glucuronic acid.

TABLE 1 below shows the examples of the structure of certain nonpolymeric layers according to the invention

| Function | Structure |
|---|---|
| phosphonate | R—CH$_2$—P(=O)(O$^-$)(O$^-$) |
| Phosphonate monoester | R—CH$_2$—P(=O)(O$^-$)(O—R') |
| phosphinate | R—CH$_2$—P(=O)(O$^-$)(R') |
| Sulfonate | R—CH$_2$—S(=O)$_2$—O$^-$ |
| hydroxamate | R—C(=O)—NH—O$^-$ |
| Siloxane | R—Si(O—)(O—)(O—) |
| catecholate | R—C$_6$H$_3$(OH)(OH) |

Advantageously, in these structures:

R' represents a linear or branched alkyl group, where appropriate substituted;

R represents an X1-L group, in which L represents a linker group (for example, linear or branched alkyl, where appropriate substituted), and X1 represents a function capable of providing the coupling (i.e. the grafting) of the nonpolymeric layer with groups that promote macrophage uptake and/or groups that facilitate BBB transfer.

Those skilled in the art clearly understand that the oxygenated groups of the above table enable the attachment of the nonpolymeric layer to the metal core of the nanoparticle according to the invention, while the R groups are intended for the coupling with the groups that promote macrophage uptake and/or groups that facilitate BBB transfer.

Advantageously, L has the definition indicated below. Advantageously, X1 has the same definition as that of X indicated below.

Preferably, the nonpolymeric layer comprises biphosphonate or gem-bisphosphonate chemical groups. It is advantageously a biphosphonate or gem-bisphosphonate layer, in particular as described in detail in document WO 2004/058275 (gem-bisphosphonate layer and associated definitions of this document incorporated by way of reference).

Advantageously, the gem-bisphosphonate layer has the formula (II):

X-L—CH(PO$_3$H$_2$)$_2$ described in WO 2004/058275, in which:

L represents an organic linker group linking the function X to the gem-bisphosphonate —CH(PO$_3$H$_2$)$_2$ function;

X represents a chemical function.

Preferably, L represents a divalent group, for example chosen from:

an aliphatic group (for example, C$_1$ to C$_5$); alicyclic group; aliphatic alicyclic group; aromatic group; aliphatic aromatic group, it being possible for said aliphatic, alicyclic and aromatic groups to be optionally substituted with a methyl, hydroxyl, methoxy, acetoxy or amido group or a halogen atom, advantageously a chlorine, iodine or bromine atom;

an -L$_1$-NHCO-L$_2$ group where L$_1$ and L$_2$, which may be identical or different, represent an aliphatic group; alicyclic group; aromatic group; aliphatic alicyclic group or aliphatic aromatic group; it being possible for said groups to be optionally substituted with a methyl, hydroxyl, methoxy, acetoxy or amido group or a halogen atom, advantageously a chlorine, iodine or bromine atom.

By way of preferred groups X, mention may in particular be made of:

—COOH, —NH$_2$, —NCS, —NH—NH$_2$, —CHO, alkylpyrocarbonyl (—CO—O-alk), acylazidyl (—CO—N$_3$), iminocarbonate (—O—C(NH)—NH$_2$), vinylsulfuryl (—S—CH═CH$_2$), pyridyldisulfuryl (—S—S-Py), haloacetyl, maleimidyl, dichlorotriazinyl and halogen, —COOH and —NH$_2$ groups being particularly preferred.

The nonpolymeric layer is such that groups that promote macrophage uptake and/or groups that facilitate BBB transfer are grafted onto this nonpolymeric layer. Thus, the following are grafted onto the nonpolymeric layer:

either groups that promote macrophage uptake, or groups that facilitate BBB transfer, or both groups that promote macrophage uptake and groups that facilitate BBB transfer.

The expression "nonpolymeric layer" is intended to mean nonpolymeric layers such as, for example, those mentioned above, different than the known polymeric layers described below (polysaccharide layers in particular). Advantageously, a nonpolymeric layer does not comprise any polymeric group. However, a nonpolymeric layer may comprise some polymeric groups, advantageously PEGs, capable of bonding directly to the metal core, and intercalated between the nonpolymeric groups of the layer. In this case, such a layer comprises less than 50% by weight of polymeric groups, advantageously between 1% and 25% by weight, even more advantageously between 1% and 20% by weight, particularly advantageously between 1% and 15% by weight, of polymeric groups. Advantageously, these polymeric groups are not polysaccharides.

A description is now given of variants of groups that promote macrophage uptake (called uptake groups) and/or groups that promote BBB transfer (called transfer groups).

Advantageously, the uptake groups (which may also, where appropriate, promote BBB transfer) are hydrophilic groups.

Advantageously, these hydrophilic groups have a molecular weight (molar mass in g/mol) of greater than 200, and are selected from the following groups:

1) Polyhydroxyalkyl;

2) (R$_2$g)$_e$[(R$_2$g)$_i$R$_3$]$_h$ where:

h=1 or 2; i=0, 1 or 2; e=1 to 5;

R$_2$ represents (the R$_2$ being identical or different):

nothing, an alkylene, an alkoxyalkylene, a phenylene, or a saturated or unsaturated heterocyclic residue, optionally substituted with OH, Cl, Br, I, (C1-C8)alkyl, (C1-C8) alkoxy, $NO_2$, $NR_XR_Y$, $NR_XCOR_Y$, $CONR_XR_Y$ or $COOR_X$, $R_X$ and $R_Y$ being H or (C1-C8)alkyl, the alkyl, alkylene and alkoxy groups, which are C1 to C14 or C1-C8, being linear, branched or cyclic and possibly being hydroxylated;

g represents (the g being identical or different): nothing or an O, CO, OCO, COO, $SO_3$, $OSO_2$, CONR', NR'CO, NR'COO, OCONR', NR', NR'CS, CSNR', $SO_2NR'$, $NR'SO_2$, NR'CSO, OCSNR', NR'CSNR', P(O)(OH)NR' or NR'P(O)—(OH) function, in which R' is H, (C1-C8)alkyl or $R_3$;

$R_3$ represents alkyl, phenyl, alkyl substituted or interrupted with one or more phenyl groups, alkyleneoxy; amino or amido which may or may not be substituted with alkyl optionally substituted or interrupted with one of the above groups;

it being possible for the phenyl, phenylene and heterocyclic groups to be substituted with OH, Cl, Br, I, (C1-C8) alkyl, (C1-C8)alkoxy, $NO_2$, $NR_XR_Y$, $NR_XCOR_Y$, $CONR_XR_Y$ or $COOR_X$, $R_X$ and $R_Y$ being H or (C1-C8)alkyl, and the alkyl, alkylene and alkoxy groups, which are C1 to C14 or C1 to C8, being linear, branched or cyclic and possibly being hydroxylated.

Preferably, these groups are alkyl, alkoxyalkyl or alkenyl groups, where appropriate interrupted with —NH—, —O—, —CO— or NH(CO)—, where appropriate coupled to at least one phenyl group, and carrying hydroxyl groups, such as alcohol or amino alcohol chains, and in particular:

1) —$CH_2$—$CH_2OH$, —CHOH—$CH_2OH$, —CH—($CH_2OH$)$_2$ or —$(CH_2)_m$—$(CHOH)_p$—$CH_2OH$, with m=1 to 5, p=1 to 5 (any combinations of m and p being possible);

2) the group of formula:

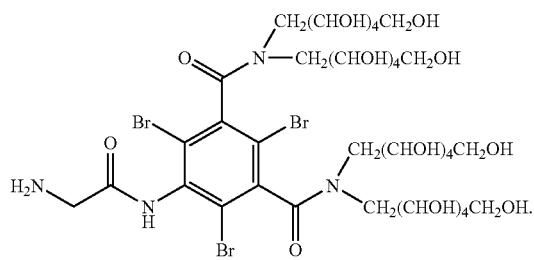

According to one embodiment, the transfer groups (capable of also promoting, where appropriate, macrophage uptake) are polymeric groups, advantageously polyoxy(C2-C3)alkylene groups (polyoxyethylenes and polyoxypropylenes), in particular polyethylene glycol (PEG) and C1 to C3 monoethers and monoesters thereof, and amino-PEGs, preferably having a molar mass of 350 to 2000. Advantageously, these groups are not polysaccharides.

Among the PEG groups, use may in particular be made of $(CH_2CH_2O)_q(CH_2)_r$—CO— and $(CH_2CH_2O)_q(CH_2)_r$—NH—CO— groups, with q=1-10 and r=2-10; for example, PEG 300, PEG 700, PEG 750, PEG 1000, PEG 1500, PEG 2000.

The grafting of the uptake groups and of the transfer groups is carried out by covalent bonding with groups of the nonpolymeric layer, by means of processes well known to those skilled in the art. For example, in the case of the amino-PEG polymeric groups and of the layers of formula II in which X represents a —COOH group, the amine function of the amino-PEG groups is coupled to the acid function of the compound (II).

The degree of grafting and the nature of the uptake groups and of the transfer groups are determined according to the desired biological and chemical properties.

According to one embodiment, this degree of grafting is less than 50% by weight and advantageously between 1% and 25% by weight, even more advantageously between 1% and 20% by weight, particularly advantageously between 1% and 15% by weight.

According to another embodiment, this degree of grafting is greater than 50%, advantageously between 70% and 95%, even more advantageously between 80% and 90%.

The nanoparticle advantageously exhibits a degree of grafting of uptake groups of between 10% and 100%, advantageously between 50% and 95%, between 60% and 90%, for example of the order of 60%, 70%, 80%, 90%. For example, 1%, 3%, 5%, 10%, 20%, 25%, 50%, 75%, 80%, 90%, 95% of its groups X (for example acid groups) are coupled to an uptake group.

According to other embodiments, the nanoparticle advantageously exhibits a degree of grafting of transfer groups of between 10% and 100%, advantageously between 50% and 95%, between 60% and 90%, for example of the order of 60%, 70%, 80%, 90%. For example, 1%, 3%, 5%, 10%, 20%, 25%, 50%, 75%, 80%, 90%, 95% of its groups X (for example acid groups) are coupled to a transfer group. The amount and the length of the transfer groups (in particular PEGs) are adjusted so as to avoid there being too much masking of the UPSIO, which would otherwise render it to stealthy with respect to the phagocytic cells.

According to advantageous embodiments, use will be made:
either of hydrophilic groups that promote uptake, in particular amino alcohols as described above, at a degree of grafting of between 10% and 100%, advantageously between 50% and 95%, between 60% and 90%, for example 60%, 70%, 80%, 90%,
PEG groups that promote transfer, at a degree of grafting of less than 50%, advantageously less than 25%, for example from 0 to 10%, for example 5% to 10%,
for both hydrophilic groups and PEG groups.

According to advantageous embodiments, uptake groups (advantageously between 50% and 95% of the possible grafting sites on the particle) and transfer groups (advantageously between 10% and 30% of the possible grafting sites on the particle) will be grafted. Those skilled in the art understand that the total degree of grafting (i.e. the degree of grafting of the uptake groups+the degree of grafting of the transfer groups) is not necessarily 100%, it being possible for the nonpolymeric layer to have functions capable of being grafted but not being so.

Table 2 below gives examples in which the degree of grafting (as %) of the amino alcohol groups and of the PEG derivatives and also the % of functions capable of being grafted but not being so, are indicated.

|  | Ex 1 | Ex 2 | Ex 3 | Ex 4 | Ex 5 | Ex 6 |
|---|---|---|---|---|---|---|
| Degree of grafting of amino alcohol groups | 95 | 60 | 40 | 80 | 70 | 20 |
| Degree of grafting of PEG derivatives | 5 | 20 | 20 | 20 | 30 | 60 |
| % of functions capable of being grafted but not being so | 0 | 20 | 40 | 0 | 0 | 20 |

Some examples of table 1 are advantageous in particular for the diagnosis of AD when the inflammatory stage is already quite advanced: the BBB allows an increased number of macrophages to pass through and the USPIO crosses the BBB at least in part by means of cells of the immune system, which makes it possible to use a higher degree of grafting of uptake groups (80% for example).

For a rather early targeting, it may be preferable to increase the portion of transfer groups (PEG groups in particular) so as to facilitate the access of the USPIOs to the sites of inflammation in the brain, in particular at the amyloid plaques. A degree of PEG grafting of between 40% and 80% may then, for example, be used.

For early targeting, high degrees of grafting of uptake groups may also be used when opening of the BBB has been facilitated (mannitol shock, for example), or when the USPIOs are encapsulated in transfer vectors described below.

The mechanism of transfer of the USPIOs carrying transfer groups has not been completely elucidated. The applicant puts forward the hypothesis that this transfer involves a biological mechanism of active and/or passive transport, via vesicles for example, or via an opsonization phenomenon.

In embodiments, the applicant has succeeded in obtaining products capable of being taken up by cells of the immune system (macrophages in particular), by virtue of their physicochemical properties (charge state, recognition by opsonins, etc.), while at the same time being capable of crossing the BBB. In particular, the PEG groups were chosen in such a way that these grafted USPIOs are not too stealthy to be taken up by macrophages.

The structure of the metal core is now described more precisely.

According to one embodiment, the core is monocrystalline, preferably based on an iron compound. Other cores such as gold or tungsten have also been studied.

It is recalled that the particles based on an iron compound advantageously comprise iron (III), generally an iron oxide or hydroxide. The core of these magnetic particles is typically composed entirely or partly of iron oxide; of iron oxide hydrate; of ferrites; of mixed iron oxides such as mixed iron oxides containing cobalt, nickel, manganese, beryllium, magnesium, calcium, barium, strontium, copper, zinc or platinum; or of a mixture thereof. The term "ferrite" denotes the iron oxides of general formula $[xFe_2O_3, yMO_z]$, where M denotes a metal that can be magnetized under the effect of a magnetic field, such as Fe, Co, Ru, Mg or Mn, it being possible for the magnetizable metal to be optionally radioactive.

Advantageously, the magnetic particles of the compositions used in the context of the invention comprise a ferrite, in particular maghemite ($yFe_2O_3$) and magnetite ($Fe_3O_4$), or mixed ferrites of cobalt ($Fe_2CoO_4$) or of manganese ($Fe_2MnO_4$).

According to embodiments, the nanoparticles comprise a polycrystalline core covered with a nonpolymeric layer. For example, the core comprises several different iron oxide crystals.

According to another embodiment, the nanoparticles comprise a core obtained from a nonsuperparamagnetic metal, in particular from an oxide of a lanthanide such as gadolinium or europium, or from other mixed crystals, the obtaining of which is described in detail, for example, in WO2006/031190.

The nanoparticles have a size typically between 2 and 200 nm, advantageously between 10 and 60 nm, advantageously of the order of 5, 10, 20, 30, 40, 50 or 60 nm. The nonpolymeric layer forms a coating of the core.

According to another aspect, the nanoparticles covered with a nonpolymeric layer devoid of AD-specific targeting biovector, but carrying uptake groups and/or transfer groups, are associated with (coupled to and/or incorporated in, advantageously incorporated in) a BBB transfer vector, this transfer vector being intended to enable and/or increase crossing of the BBB by the nanoparticles.

Among the BBB transfer vectors, mention will be made of:
lipid vectors such as liposomes, emulsion systems, micelles, mixed liposome-micelle systems;
suitable surfactants, capable of forming a coating or a protective capsule around the metal nanoparticle, for example chosen from the following: esters of fatty acids and glycerol, sorbitol and other multifunctional alcohols, glycerol monostearate, sorbitan monolaurate, sorbitan monooleate, poloxamines, polyoxyethylene ethers and polyoxyethylene esters, ethoxylated triglycerides, ethoxylated phenols and diphenols, GENAPOL surfactant, metal salts of fatty acids, sodium lauryl sulfate, sodium dodecyl sulfate, metal salts of sulfosuccinates, polysorbates, poloxamer, polyoxyethylene glycols, poly (butyl cyanoacrylate), TWEEN, polylactic acid (PLA) homopolymer and/or poly(lactic-co-glycolic acid) (PLGA) heteropolymer;
transport macromolecules such as proteins, in particular lipoproteins.

For the liposomes, use will, for example, be made of sphingolipids, glycolipids, glycerolipids, phospholipids, and cholesterol. Use will, for example, be made of the following compounds: phosphatidic acid, phosphatidylcholine, phosphatidylserine, phosphatidylglycerol, phosphatidylethanolamine, phosphatidylinositol, cardiolipid; neutral phospholipids such as dipalmitoyl phosphatidylcholine (DPPC), dimyristoyl phosphatidylcholine (DMPC), dilauroyl phosphatidylcholine (DLPC), dioleoyl phosphatidylcholine (DOPC), phosphatidylcholine (PC), distearoyl phosphatidylcholine (DSPC), sphingomyelin (SM), monosialoganglioside and sulfogalactosylceramide. Pegylated liposomes may advantageously be used.

The preparation of liposomes is known from the prior art and is, for example, described in U.S. Pat. No. 5,643,599 and WO 2006115416, using the customary film hydration technique. Such documents describing the preparation of liposomes are incorporated by way of reference.

According to variants, the BBB transfer vectors are capable of crossing the BBB at least in part via lipid receptors.

Advantageously, the BBB transfer vectors are able to release the nanoparticles according to the invention once the BBB has been crossed, where appropriate after activation, for example chemical or physical activation (temperature, ultrasound, etc.). Thermosensitive liposomes capable of releasing the USPIOs and optionally a therapeutic active ingredient also included in the liposome will, for example, be used.

According to another aspect, the BBB transfer vector that can be used in the context of the present invention comprises, advantageously carries, an AD-targeting biovector, advantageously an AD-specific targeting biovector. Among the possible AD-targeting biovectors, benzothiazoles, or the peptides (Ass,Apl, for example) of WO 2094191 will be used. Mention will also be made of AD-targeting biovectors described in the prior art in diagnosis or in therapy, for example: benzodiazepines, thiophenes, furans, pyrrole, pyrazole, ligands limiting the formation of Abeta peptides, anti-Abeta antibodies, ligands that interact with glutamate receptors, such as sulfanamides, compounds of 1-aminocyclohexane type, secretase inhibitors; other biovectors identified as modulating an enzyme mechanism and/or a mechanism of synthesis associated with AD, for example for targeting secretases; other biovectors identified as capable of modulating or monitoring the activity of neurotransmitters.

It is thus possible to also use biovectors identified (peptides in particular for targeting plaques or NFTs or identified precursors of these plaques and NFTs) as capable of early recognition of AD, including, where appropriate, those which up until now were not selected for the diagnosis of AD owing to their difficulty in crossing or in their inability to cross the BBB in the absence of this transfer vector.

Where appropriate, the diagnostic composition according to the invention comprises, in addition to the nanoparticles according to the invention detectable in diagnostic imaging, at least one therapeutic agent against AD. In particular, in the case of the nanoparticles associated with a BBB transfer vector, the therapeutic agent against AD is associated with said BBB transfer vector. Advantageously, it is incorporated into the BBB transfer vector.

According to embodiments, the diagnostic composition according to the invention also comprises an agent for facilitating passage across the BBB, such as mannitol or other appropriate compounds, in particular when the diagnostic composition is administered at a not very advanced stage of the AD.

According to another aspect, the invention relates to multimodal imaging using compositions described above for MRI, combined with other modes of imaging, such as advantageously, for example, MPI, PET imaging with compounds known for PET imaging of Alzheimer's disease (for example, a biomarker that is a ligand for amyloid plaques, coupled to a chelate labeled with technicium, gallium or any other radionuclide), X-ray scanning, MRI imaging with gadofluorines, optical imaging, fluorescence imaging, or SPECT imaging, in particular perfusion SPECT imaging. In addition, the imaging may be combined with various modes of cerebral mapping, CBV (cerebral blood volume) for example. All these various modes typically comprise image processing methods and systems, analyzing and, where appropriate, regulating the administration of contrast product or of therapeutic treatment as a function of data from the patient, and of databases on AD patients.

Among the various diagnostic subindications for the diagnosis of Alzheimer's disease, mention will be made not only of diagnosis at the advanced stage (typically with inflammation), but also of diagnosis at an early stage or diagnosis at an intermediate stage such that they make it possible to establish or confirm a level of pathological risk and, where appropriate, to monitor the effectiveness of an early and/or late therapeutic treatment against the disease (drug or drug candidate still at the preclinical stage or at the clinical trials stage). The applicant has in fact identified macrophage uptake as a means of access to the pathological regions, but it is possible that other mechanisms enable or facilitate the crossing of the BBB by the nanoparticles described.

According to another aspect, the invention relates to the use of the nanoparticles mentioned in the application, for the preparation of a diagnostic composition for the diagnostic monitoring of the effectiveness of a drug or a drug candidate against Alzheimer's disease (and a method of diagnosis or of diagnostic monitoring of a therapeutic treatment using the nanoparticles above).

As regards more specifically the use of the compounds described for monitoring therapeutic treatment of AD, at least one therapeutic drug or therapeutic agent against Alzheimer's disease and at least one contrast agent of the application are administered in the same composition or in separate compositions, simultaneously or sequentially.

Advantageously, the contrast agent makes it possible to rapidly identify the effectiveness of the treatment, and makes it possible to more appropriately target the most suitable therapeutic treatment. For example, the therapeutic treatment comprises, at the beginning, a step of administering the therapeutic drug and the diagnostic agent (USPIO of the applicant), and then, depending on the first result obtained, orientation of the subsequent therapy by continuing this treatment or by choosing another treatment (more economical and/or effective taking into account the database of results obtained in similar cases).

The therapeutic compounds (therapeutic drug or agent) concerned are all those known for the treatment of AD, and are advantageously chosen from the list which follows (the patent references between parentheses are examples of compounds, without limiting the invention to these examples):

- modulators of an enzyme mechanism (secretases, etc.) and/or of transduction and/or modulator of a signaling pathway known for AD;
- compounds capable of modulating the cellular processing of beta-amyloid precursor protein (APP) and for the prevention or treatment of diseases associated with abnormal processing of APP (WO2007132292);
- peptides capable of binding to amyloid plaques (WO2007145589);
- anti-inflammatory cytokines (WO2007139178);
- isoxazole derivatives (WO2007137954);
- pyrazinone derivatives (WO2007135131);
- pyridazines and other secretase inhibitors (and cholinesterase inhibitors) which are intended for the modulation of cell pathways (for example, of signal transduction pathways) (WO2007130383);
- sulfonamide inhibitors of gamma secretase (WO2007143523);
- piperidine modulators of gamma secretase (WO2007125364);
- presenilin/G-protein/c-src binding polypeptides involved in signaling mechanisms implicated in Alzheimer's disease (WO2007123680);
- acetylcholinesterase inhibitors (WO2007122274);
- 2-aminopyrimidin-4-ones (WO2007114771);
- amide or ester derivatives of hydroxyethylamine that serve as effective beta-secretase inhibitors (WO2007110727);
- antagonists of the histamine 3 receptor (tetralines, for example) (WO2007105053);
- inhibitors of Apolipoprotein E receptors (WO2007098417);
- indazole derivatives (WO2007088401);
- regulators of the ADAMTS4 protein (WO2007088399);
- G protein-coupled receptor antagonist;
- metabotropic glutamate receptor (mGluR) antagonists;
- fluoro substituted 2-oxo azepan secretase inhibitors (WO2007020190);
- malonamide derivatives (WO2007110335);
- tetraline and indane derivatives which are 5-HT6 and/or 5-HT2A antagonists (WO2006066790);
- 2-imidazoles (WO2007090720);
- arylsulfonyl benzodioxanes for modulation of 5-HT6 and 5-HT2A receptors (WO2005105776);
- Phosphinic acid derivatives which are beta-secretase inhibitors (WO2005044830);
- tetrahydrocarbazoles and derivatives for the treatment of diseases associated with LXRalpha and/or LXRss agonists (WO2005092856);
- substituted dibenzoazepine and benzodiazepine derivatives which are gamma-secretase inhibitors (WO2005040126);

benzoxazepinone derivatives (WO2004100958);
thiazolopyridine derivatives which are adenosine receptor ligands (WO2005028484);
histamine H3 receptor antagonists: ether histamine-3 (WO2007138431), azabicyclic tetralines (WO2007105053), benzimidazole (WO2007069053), imidazoles for inhibiting the production of Ass peptide (WO2007034326);
thiazole sulfonamide compounds that are inhibitors of Abeta peptide production (WO2005097114);
thiazole amines (WO2005095367, WO2005095368), oxazole amines (WO2005095365), pyrazole amine (WO2005095348), isothiazole and isoxazole amine (WO2005095361);
any compound against inflammation in Alzheimer's disease, for example COX-2 inhibiting agents, for example sulfonyl pyrazoles, for example heterocyclo-alkylsulfonyl pyrazoles (WO03037351);
cyclosporin compounds (WO2006005580);
any agent having an activity on VEGFR-2, Tie-2, c-Src, c-Met, FGFR-1, Flt-1, HER-2, c-Abl, c-Raf, PDGFR-beta protein kinases, having an effect against amyloid plaques, for example pyridinylpyrimidinylaminobenzamide compounds (WO2005039586);
anti-beta-amyloid vaccine (WO2005014041);
any targeting compound that modulates GABA receptors, in particular the following compounds:
   aryl-4-ethynylisoxazole derivatives with affinity and selectivity for GABA A a5 receptor sites (WO2007137954);
   arylisoxazol-4-ylimidazo[1,2-a]pyridine derivatives (WO2007082806);
   isoxazol-4-yloxadiazole derivatives (WO2007071598);
   imidazobenzodiazepine derivatives; imidazo[1,5-a][1,2,4]triazolo[1,5-d][1,4]benzodiazepine (WO2007042421, WO2006045430).

The mean hydrodynamic diameter of the basic structure of the USPIO used (iron oxide core covered with the layer) in solution is typically between 2 and 500 nm. Advantageously, at least 90% of the particles present, and preferably at least 95% of the particles present, are individualized particles, i.e. particles not agglomerated with one or more other particles. The mean hydrodynamic diameter to which reference is made here is the mean hydrodynamic diameter as measured by photon correlation spectroscopy, for example using a Zetasizer instrument.

The relaxivities r1 and r2 of a magnetic contrast product give the measure of its magnetic effectiveness and make it possible to assess its influence on the signal recorded. The compounds obtained have advantageous relaxivities r1 and r2, making it possible to obtain a large increase in the proton relaxation rates (R1=1/T1 and R2=1/T2). This effect on the relaxation rates then makes it possible to obtain a good contrast in MRI, in the targeted regions. The relaxivity r1 is of the order of 10 to 50 mMol$^{-1}$ s$^{-1}$ and the relaxivity r2 is of the order of 20 to 400 mMol$^{-1}$ s$^{-1}$, at 20 Mhz. The iron content of the particle (% by weight) is of the order of from 20% to 60%, typically from 30% to 50%.

The diagnostic composition administered typically comprises one type of nanoparticles, but several different nanoparticles may also be used in combination, simultaneously or sequentially.

The present application provides examples of models for testing the diagnostic effectiveness of the compound comprising nanoparticles.

The USPIOs are typically used at a dose of typically from 0.001 mol/kg to 10 mmol/kg with respect to metal, for example from 1 mol/kg to 5 mmol/kg, by injection or infusion in an artery or a vein.

The USPIOs are typically in the form of stable colloidal solutions (or of stabilized particle suspensions) and can be formulated in the form of lyophilized powders to be combined with an appropriate solvent. The route of administration thereof is known to those skilled in the art, typically intravenous.

The compositions of the invention are preferably administered parenterally, the other routes of administration not, however, being excluded, administration in the form of an intravenous injection being particularly preferred. The injection is typically given as an i.v. bolus, where appropriate as an intracarotide injection, with, if necessary, an osmotic shock with mannitol so as to promote opening of the BBB. An intracerebral injection may also be carried out.

The forms for parenteral administration are obtained conventionally by mixing the magnetic particles with buffers, stabilizers, preservatives, solubilizing agents, isotonic agents and suspending agents. In accordance with the known techniques, these mixtures are subsequently sterilized and then packaged in the form of intravenous injections or of lyophilizates ready to be reconstituted in a pharmaceutically acceptable sterile carrier.

The unit doses will depend on the composition of the magnetic particles, on the route of administration, on the type of diagnosis to be established, and also on the patient. The unit doses will, in general, be 1-10 mmol of iron for a person of average weight (75 kg). Among the pharmaceutical adjuvants, mention may be made of preservatives, pH stabilizers and antioxidants.

It is interesting to note that such compounds of the application with an anionic or polymeric layer can also be used for indications other than AD, such as cardiovascular diseases (atheroma, atherosclerosis, etc.) or inflammatory diseases or cancer diseases.

Moreover, the applicant has studied the comparison, for the diagnosis of AD, of particles obtained with nanoparticles comprising a monocrystalline core covered with a polymeric layer, advantageously a polysaccharide polymeric layer, or a nonsaccharide polymeric layer; the polysaccharide being in particular chosen from dextran and known derivatives thereof, starch (and known derivatives thereof, for example hydroxyethyl or hydroxymethyl starch); the nonsaccharide polymer being in particular a polymer or a copolymer chosen from: polyalkylene glycols, in particular polyethylene glycol, polypropylene glycol, polyglycerol and polyoxyethylene, stearate derivatives, poly(alkyl cyanoacrylate)s, polyvinyl compounds, cyclodextrins, pectins, glycosaminoglycans, cellulose derivatives and heparin, and derivatives of these various polymers or copolymers. The nanoparticles may comprise several successive polymeric layers.

As an advantageous particle for the diagnosis of AD, mention will in particular be made of nanoparticles described in WO2006012201, WO2006/031190, US2005/0260137, or WO2004/107368.

The applicant has also studied the use of nanoparticles covered with a polymeric or nonpolymeric layer mentioned in the above application, and coupled to at least one AD-specific targeting biovector (for example peptide or antibody as indicated above), these nanoparticles being associated with (incorporated in or coupled with) a BBB transfer vector such as those indicated above. The products thus obtained are particularly advantageous when a targeting biovector capable of detecting AD preferably early is used.

The applicant has thus studied the grafting to these nanoparticles of chemical groups such as biovectors (peptides, for example) capable of targeting regions affected by Alzheimer's disease, these biovectors possibly being intended to facilitate crossing of the BBB.

The applicant has also studied compounds comprising, grafted to the nanoparticles, on the one hand, at least one biovector for targeting affected regions and, on the other hand, at least one ligand for crossing the BBB, such as a peptide or other suitable compound.

The detailed description which follows illustrates detailed embodiments of compounds and results for the diagnosis of Alzheimer's disease.

Figure 1:
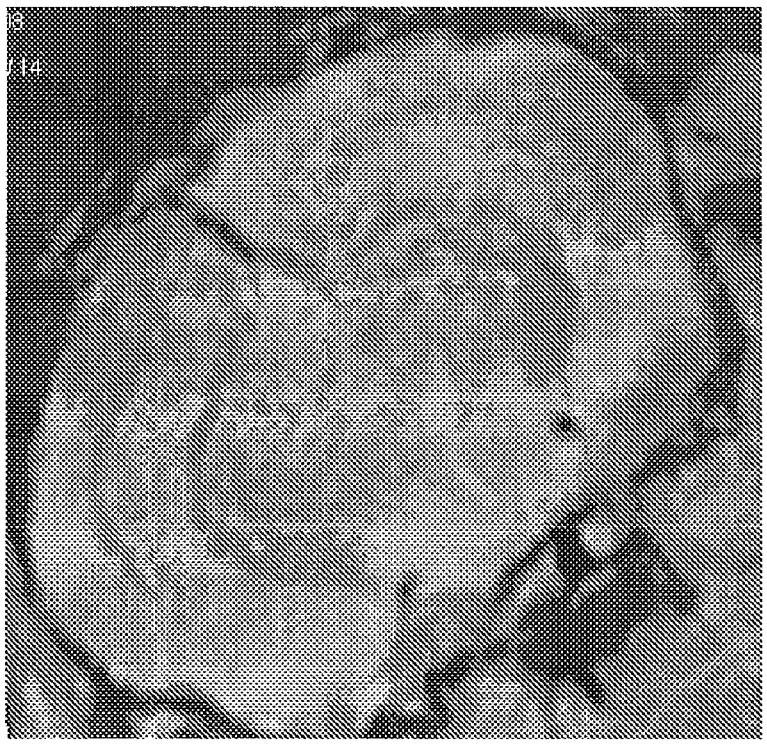
FIG. 1 represents an example of an in vivo NMR image pre-injection.
Figure 2:
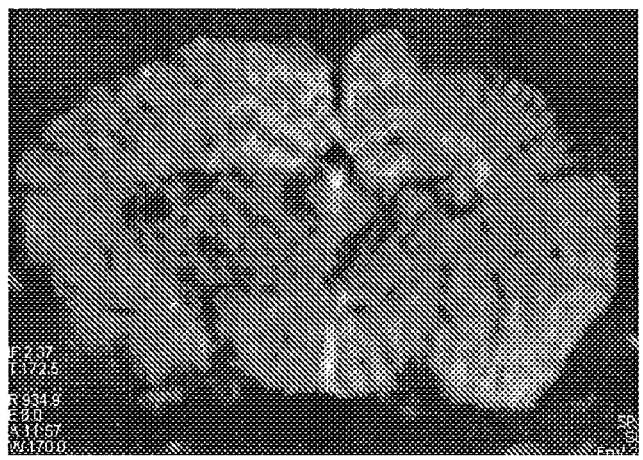
FIG. 2 represents an example of in vivo NMR images post-injection, obtained at 36 h after injection of the compound according to example I using the protocol according to example IV.

I. Example of a nanoparticle covered with a nonpolymeric layer: gem-bisphosphonate layer with hydrophilic branch $AAG_1AA_{28}Br$ (macrophage uptake group).

This compound is obtained as in example 16 of WO 2004/058275. It has the following formula:

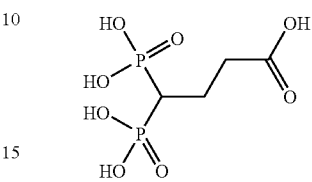

The process for the preparation thereof is therefore the following: 0.853 g ($7.6 \times 10^{-4}$ mol) of compound E of example 5 of WO2004/058275 is dissolved in 13.55 ml of example 11 of WO2004/058275 at 0.279 M/L. The pH is adjusted to 6.2.

171 mg of 1-(3-dimethylaminopropyl)-3-ethylcarbodiimide hydrochloride are added. The whole is stirred at ambient temperature for 24 hours. The solution is ultrafiltered through a PALL®-brand stirring cell having a cutoff threshold of 30 kD. 5 00 ml of filtrate are eliminated. The retentate is adjusted to 30 ml.

Compound E of example 5 of WO2004/058275: (N,N'-[bis (2,3,4,5,6-pentahydroxyhexyl)]-2,4,6-tribromo-5-(glycylamino)isophthalamide, denoted $AAG_1AA_{28}Br$ (AA signifying amino alcohol), has the following formula:

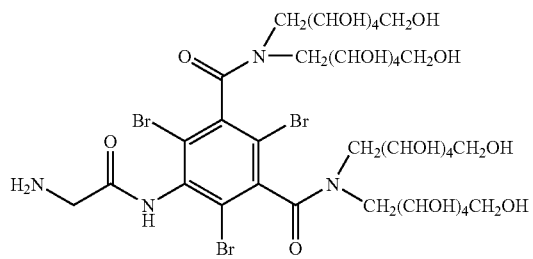

It is prepared according to the procedure described in EP 0 922 700 A1.

The solution of example 11 of WO2004/058275 is prepared in the following way: 50 ml of example 8 of WO2004/058275 at 4.73 M/L are diluted in 3 liters of water. A solution of 1.3 g ($5.24 \times 10^{-3}$ mol) of compound A of example 1 of WO2004/058275 in 80 ml of water is introduced dropwise. The formula of compound A of WO2004/058275 is the following:

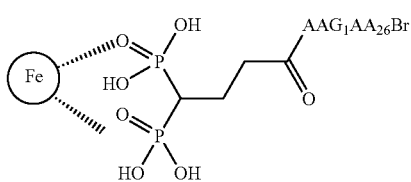

Stirring is maintained for 30 min. The flocculate is isolated by magnetic separation and is then washed 3 times with 3 liters of water. It is redissolved with 700 ml of water at pH 11 with a sufficient quantity of NaOH [1N], and then stabilized at pH 7.2 with a sufficient quantity of HCl [1N]. The final solution is filtered through a 0.22 μm membrane.

The characteristics of the compound of example 16 of WO2004/058275 are the following:

[Fe]=0.132 M/L PCS size=41.6 nm Poly σ=0.22

Fe=52.3% Mass/Mass; P=0.77% Mass/Mass; C=5.86% Mass/Mass; Br=2.65% Mass/Mass;

Degree of grafting [compound A/Fe]=1.33% mol/mol

Degree of grafting [compound E/Fe]=1.18% mol/mol

Degree of grafting [compound E/compound A]=89%.

II. Demonstration of the Uptake by Macrophages of the Nanoparticles Obtained in Example I The gem-bisphosphonate compound responds positively to the phagocytosis test on activated THP1 cells (macrophages), with an unexpected uptake of about double that of SINEREM®-brand ultrasmall superparamagnetic iron oxide (20 μg iron/$10^7$ C, instead of 8 μg iron/$10^7$ C for SINEREM®-brand ultrasmall superparamagnetic iron oxide shown by means of the following test:

Protocol

Flasks of 225 cm² are seeded with THP-1 cells.

D0

110 ml of RPMI+10% FCSi+122 μL of $10^{-4}$ M PMA, i.e. a final concentration of 25 nM, are prepared.

The THP-1 cells are counted and then $110 \times 10^6$ thereof are centrifuged. The supernatant is removed and the pellet is taken up with 60 ml of PMA supplemented medium.

After homogenization, 5 ml are distributed into wells of 6-well plates (5 ml/well), denoted 1 to 21=activated THP-1 cells.

D1

In the activated THP-1 plates (wells 1 to 21): the supernatant is removed and 5 ml/well of PBS-10% FCSi are distributed.

D2

Each cell layer is scraped with a blue pipette tip.

The suspension is placed in a tube (15 ml flask).

The wells are rinsed twice with approximately 2 ml of PBS, which is added to the suspension. The entire suspension is poured onto 5 ml of PERCOL (diluted to ½ in PBS) (15 ml flask).

Centrifugation is carried out for 10 minutes at 1200 rpm, acceleration and deceleration at 2, temperature at 20.degree. C. (SIGMA 3K15 or MEGAFUGE 1.0R without brake).

The cells are carefully recovered from the cell ring, in a 15 ml flask.

Each tube is made up to 15 ml with PBS.

The cell suspension is counted.

The suspension is centrifuged at 1400 rpm for 5 minutes, acceleration and deceleration at 7 (SIGMA 3K15 or MEGAFUGE 1.0R with brake), and then the supernatant is removed.

The cell pellets are stored at −20° C. for assaying of the iron by ICP-SEA.

III. Examples of Suitable Alzheimer Models for Confirming the Effectiveness of the Nanoparticles Use is, for example, made of transgenic mouse models that develop Aβ plaques and NFTs, and are described in:

"Tau and transgenic animal models" J. Götz. Brain Research Reviews. (2001)

"Animal models of cognitive dysfunction." S. K. Tayebati. Mech. of Ageing and Dev. (2006);

"Transgenic mouse models of AD: how useful have they been for therapeutic development?" K. Duff and S. Suleiman. Briefing in Functional Genomics and Proteomics (2004);

"Triple-transgenic model of AD with plaques and tangles: intracellular Aβ and synaptic dysfunction". S. Oddo et al. Neuron. (2003);

the Tg2576 APP model, Hsiao et al, Science, 1996;

models described in J. Alzheimer. Dis., 9, 135-149, Mice models transgenic approaches, 2006, Games.

Use is, for example, made of models of transgenic rats obtained after incorporation of Tau protein, capable of generating the symptoms of Alzheimer's disease.

Use is, for example, made of rabbit models using the injection of aluminum maltolate (neurotoxic agent) generating the formation of Tau-positive, Aβ-immunopositive intraneural neurofilament aggregates, and described in: "A new insight on Al-maltolate-treated aged rabbit as Alzheimer's animal model". N. M. Bharathi et al. Brain Research Reviews. (2006).

Use is, for example made of primate models described in:

"Alzheimer's Aβ vaccination of Rhesus monkeys (Macaca mulatta)." S. Gandy et al. Mech. of Ageing and Dev. (2004);

"Emerging prospects for the disease-modifying treatment of AD". L. C. Walker et al. Bioch. Pharmacol. (2005).

IV. Method and Results for Imaging of Alzheimer's Disease with Nanoparticles According to Example I The nanoparticle dose injected intravenously is of the order of 100 to 2000 μmol Fe/kg, depending on the animal species studied (for example, mice, rats, monkeys).

A pre-injection imaging is carried out as a control. The NMR imaging of the nanoparticles is carried out between 1 h and 7 days post-injection depending on the dose and the species selected. The delay allows uptake of the nanoparticles and elimination of the blood contribution.

The images are done on MRIs with static magnetic fields ranging between 1.5 T (clinical field) and 20 T (pre-clinical field), under in vivo and/or ex vivo conditions.

The exploitation of the MRI results is carried out by signal analysis and/or by counting of hyper or hypo signals, depending on the NMR technique used.

The NMR sequences may be spin echo sequences or gradient echo sequences. The spatial resolution may be very high spatial resolution (200 to 30 μm in the plane) for direct visualization of the nanoparticles or an intermediate spatial resolution (1000 to 200 μm) for indirect visualization, depending on the type of sequence used. The slice thickness may be between 5 mm and 50 μm depending on the animal species and the sequence used. A small slice thickness makes it possible to have less of a partial volume, and a large slice thickness makes it possible to obtain a greater susceptibility effect.

The NMR imaging sequences are, for example, conventional gradient echo sequences, spin echo sequences, positive-contrast sequences (IRON, GRASP, ONRES, etc.), quantitative sequences (T1, T2 T2* mapping), sequences using the signal phase (for example SWI, Susceptibility Weighted Imaging), sequences derived from high-resolution spectroscopy (double quantum), sequences with preparatory modules for obtaining a better contrast (for example, an inversion-recovery module, such as the sequence using radiation dumping).

The validation of the target can be carried out by histology, by labeling of the iron or of the macrophage or microglial activity or by means of another imaging technique such as fluorescence.

Example of Protocol Used:

Animal:

This protocol is carried out on APP/PS1 double-transgenic mice 12 to 18 months old. The particle is injected i.v. at a dose of between 100 and 1000 μmol of iron/kg. The post-injection imaging was carried out at least 24 h after the injection.

Imaging:

It was carried out at 7 T. The acquisition sequence is a 3D gradient echo of 40 min and 12 h respectively under in vivo and ex vivo conditions. The resolution is 50×50×(300-100) μm³. The same sequence was applied before and after the injection.

The invention claimed is:

1. A method for diagnosing Alzheimer's disease (AD) by MRI comprising:

(a) administering to a patient in need thereof an effective amount of metal nanoparticles which comprise a metallic core covered with a nonpolymeric layer selected from phosphate, phosphonate, phosphonate monoester, bisphosphonate, diphosphonate, gem-bisphosphonate, diphosphate, thiophosphate, thiophosphonate, polyphosphate, phosphinate, sulfonate, bisulfonate, hydroxamate, arginine hydroxamate, silane, silica derivative, silanetriol, trialkoxysilane, siloxane, amino acid, mercapto, dimercaptosuccinic acid, carboxylate, aliphatic dicarboxylic or polycarboxylic acid, cyclohexanetricarboxylic acid, cyclohexanehexacarboxylic acid, or catecholate, wherein said nonpolymeric layer is grafted to a group of formula

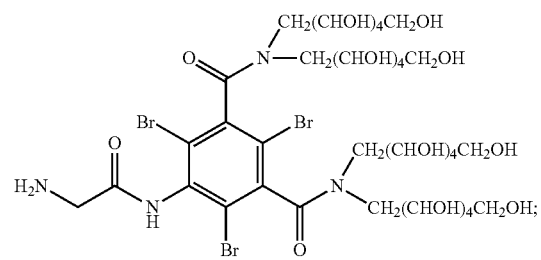

and (b) conducting a step of MRI imaging the patient to detect the metal nanoparticles.

2. The method as claimed in claim 1, wherein the metallic core is monocrystalline.

3. The method as claimed in claim 1, wherein the nonpolymeric layer is a bisphosphonate or gem-bisphosphonate layer.

4. The method as claimed in claim 1, wherein the nonpolymeric layer is a carboxylate or aliphatic dicarboxylic or polycarboxylic acid layer.

5. The method as claimed in claim 1, wherein the nonpolymeric layer has the formula:

in which:
- L represents an organic linker group linking the function X to the gem-bisphosphonate —CH(PO$_3$H$_2$)$_2$ group, chosen from an aliphatic group, alicyclic group, aliphatic alicyclic group, aromatic group, aliphatic aromatic group, it being possible for said aliphatic, alicyclic and aromatic groups to be optionally substituted with a methyl, hydroxyl, methoxy, acetoxy or amido group or a halogen atom, or an -L$_1$-NHCO-L$_2$ group where L$_1$ and L$_2$, which may be identical or different, represent an aliphatic group, alicyclic group, aromatic group, aliphatic alicyclic group or aliphatic aromatic group, it being possible for said groups to be optionally substituted with a methyl, hydroxyl, methoxy, acetoxy or amido group or a halogen atom; and
- X represents a COOH, —NH$_2$, —NCS, —NH—NH$_2$, —CHO, alkylpyrocarbonyl, acylazidyl, iminocarbonate, vinylsulfuryl, pyridyldisulfuryl, haloacetyl, maleimidyl or dichlorotriazinyl group or a halogen atom.

6. The method as claimed in claim 1, wherein the metal nanoparticles are incorporated into a blood-brain barrier (BBB) transfer vector.

7. The method as claimed in claim 6, wherein the BBB transfer vector comprises an AD-targeting biovector.

8. The method as claimed in claim 6, wherein the BBB transfer vector is able to release the metal nanoparticles after physical or chemical activation.

9. The method as claimed in claim 6, wherein the BBB transfer vector is a liposome or a surfactant.

10. The method as claimed in claim 6, wherein a therapeutic agent against AD is incorporated into the BBB transfer vector.

11. The method as claimed in claim 1, wherein the metal nanoparticles are incorporated in a diagnostic composition which comprises an agent for facilitating passage across the BBB.

12. The method as claimed in claim 1, wherein the MRI imaging is combined with at least one other imaging mode.

13. The method as claimed in claim 1, wherein the diagnosis is for monitoring the effectiveness of a drug or a drug candidate against Alzheimer's disease.

14. The method as claimed in claim 4, wherein the nonpolymeric layer is a malic acid, citric acid, tartaric acid or gluconic acid layer.

15. The method as claimed in claim 7, wherein the AD-targeting biovector is a biovector for early targeting of AD.

16. The method as claimed in claim 12, wherein the other imaging mode are optical imaging, PET imaging, X-ray scanning, SPECT imaging and/or fluorescence imaging.

* * * * *

UNITED STATES PATENT AND TRADEMARK OFFICE
CERTIFICATE OF CORRECTION

PATENT NO.         : 8,349,293 B2
APPLICATION NO.    : 12/532353
DATED              : January 8, 2013
INVENTOR(S)        : Claire Corot It is certified that error appears in the above-identified patent and that said Letters Patent is hereby corrected as shown below:

In the Specifications

At column 4, lines 27-28, change "alkylpyrocarbonyl (—CO—O-alk)" to --alkylpyrocarbonyl (—CO—O—CO-alk)--.

At column 13, in the formula at lines 30-38, change the moiety "$AAG_1AA_{26}Br$" to --$AAG_1AA_{28}Br$--, so that the formula reads as follows:

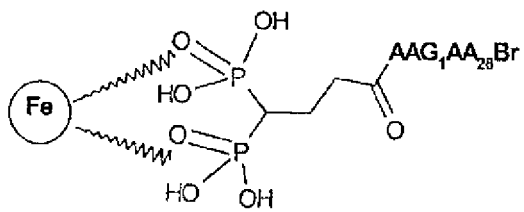

At column 14, line 62, change "PERCOL" to --PERCOLL--.

Signed and Sealed this
Eleventh Day of June, 2013

Teresa Stanek Rea
*Acting Director of the United States Patent and Trademark Office*